(12) United States Patent
Dascanio et al.

(10) Patent No.: US 7,435,241 B1
(45) Date of Patent: Oct. 14, 2008

(54) FLUID DISPENSER CLOSURE INCLUDING TUBE HAVING HYDROPHILIC AND HYDROPHOBIC PORTIONS

(76) Inventors: Gustavo A. Dascanio, 2030 Viborg Rd., Solvang, CA (US) 93463; M. Edmund Ellion, 3660 Woodstock Rd., Santa Ynez, CA (US) 93460

(*) Notice: Subject to any disclaimer, the term of this patent is extended or adjusted under 35 U.S.C. 154(b) by 642 days.

(21) Appl. No.: 10/830,364

(22) Filed: Apr. 21, 2004

Related U.S. Application Data

(63) Continuation-in-part of application No. 10/078,556, filed on Nov. 17, 2001, now Pat. No. 6,752,793.

(51) Int. Cl.
*A61H 33/04* (2006.01)
*A61M 35/00* (2006.01)

(52) U.S. Cl. .......... 604/302; 604/294; 604/295; 604/300

(58) Field of Classification Search .......... 604/295, 604/294, 300, 302
See application file for complete search history.

(56) References Cited

U.S. PATENT DOCUMENTS

| | | | | |
|---|---|---|---|---|
| 3,881,527 A | * | 5/1975 | Shapiro | 141/24 |
| 3,958,045 A | * | 5/1976 | Coleman | 427/230 |
| 5,611,788 A | * | 3/1997 | Marchment | 604/295 |
| 5,798,119 A | * | 8/1998 | Herbig et al. | 424/473 |
| 6,398,766 B1 | * | 6/2002 | Branch | 604/302 |
| 2003/0150448 A1 | * | 8/2003 | Bacon et al. | 128/200.23 |

OTHER PUBLICATIONS

Tygon Tubing Product Information brochure, www.smallparts.com/pdf/682.pdf.*

* cited by examiner

*Primary Examiner*—Tatyana Zalukaeva
*Assistant Examiner*—Melanie J Hand
(74) *Attorney, Agent, or Firm*—Hugh P. Gortler

(57) ABSTRACT

A fluid dispenser closure includes a tube having a distal end. The tube has a hydrophilic portion and a hydrophobic portion. The hydrophobic portion has an exit orifice at the distal end.

20 Claims, 7 Drawing Sheets

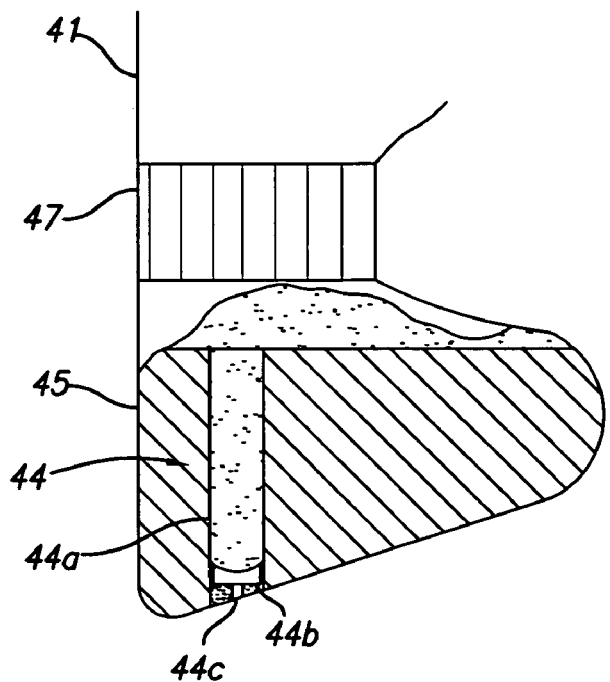
FIG. 5
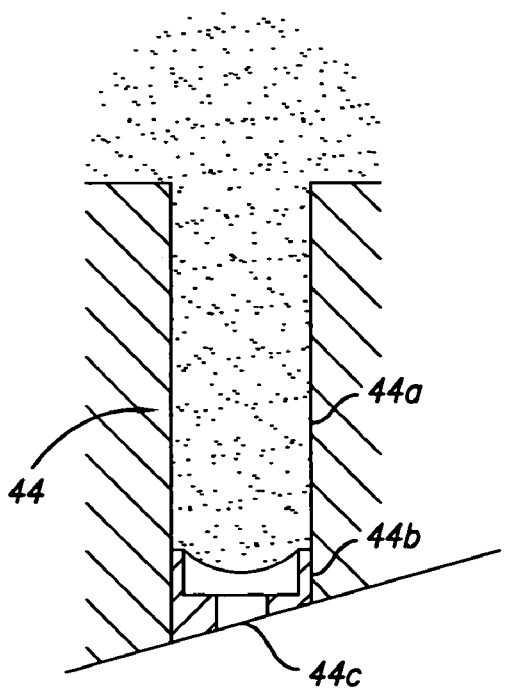 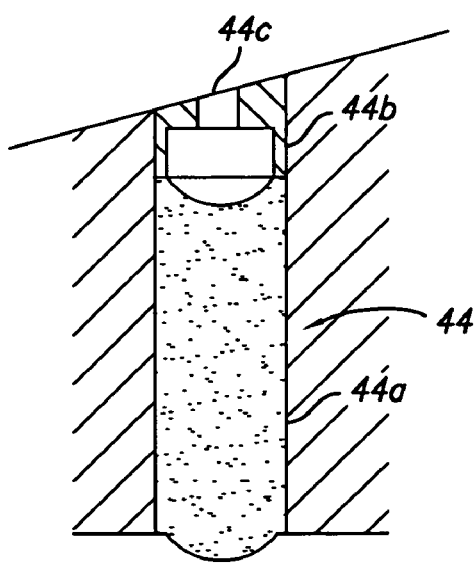
FIG. 6a  FIG. 6b

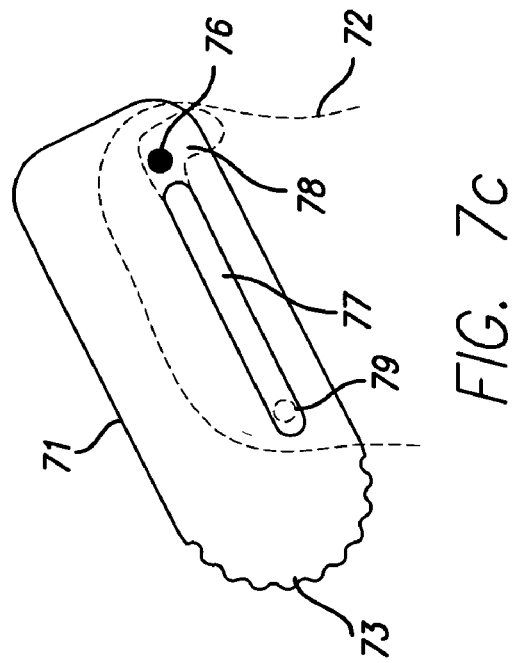
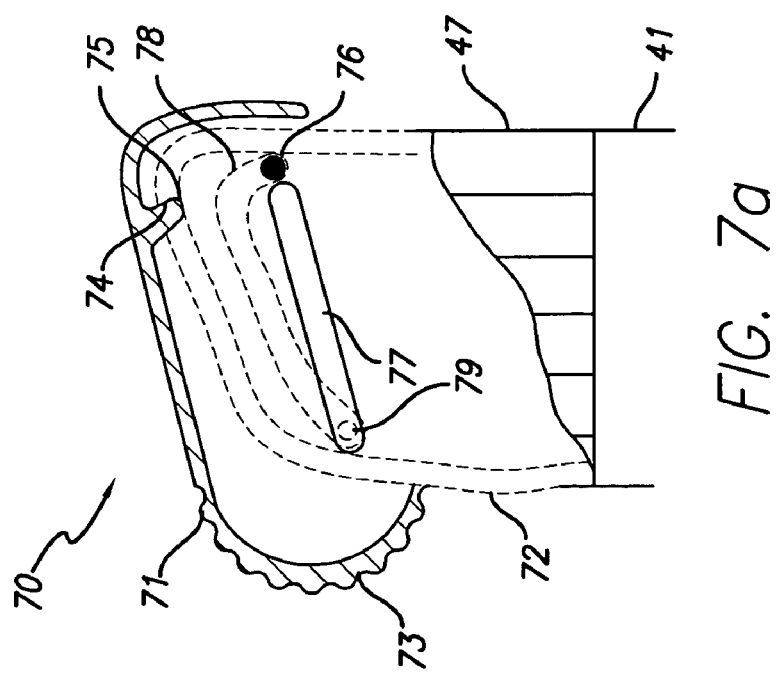
FIG. 7b
FIG. 7c
FIG. 7a

FLUID DISPENSER CLOSURE INCLUDING TUBE HAVING HYDROPHILIC AND HYDROPHOBIC PORTIONS

This is a continuation-in-part of U.S. Ser. No. 10/078,556 filed Nov. 17, 2001, now U.S. Pat. No. 6,752,793.

BACKGROUND

Many people insert eye drop liquids into their eyes for medicinal purposes or to lubricate contact lenses. While it is important to place the drop accurately to avoid waste of the expensive liquid, many people have difficulty in applying the liquid while positioning their eyelids and tilting their heads in a backward position.

Several patents describe commercially available squeeze dispensers with positioning attachments to aid in directing the eye drop into the eye. Dispensers are disclosed in U.S. U.S. Pat. Nos. 4,471,890; 4,834,728; 4,960,407; 5,366,448; 5,516,008; 5,578,020; 5,665,079; 5,810,794; 6,090,086 and 6,135,985. The dispensers in these patents have one or more of the following deficiencies: there is no control of the quantity of medication that is dispensed during each squeezing of the bottle; there is no aid in positioning the eyelid for the application of the liquid; liquid at the bottom of the container is not dispensed; the user's head must be held in an uncomfortable position; the dispenser exit is not protected from contamination during non-use; and one hand is required to position the eyelid and the other hand to squeeze the device.

SUMMARY

A fluid dispenser closure includes a tube having a distal end. The tube has a hydrophilic portion and a hydrophobic portion. The hydrophobic portion has an exit orifice at the distal end.

BRIEF DESCRIPTION OF THE DRAWINGS

FIG. 5 illustrates the eye drop dispensing device in an inverted position to fill the hydrophilic portion of the dispensing tube.

FIG. 6a is an enlarged cross-sectional view of the dispensing tube in an inverted position.

FIG. 6b is an enlarged cross-sectional view of the dispensing tube in an upright position when filled with liquid.

FIG. 7a illustrates an eye drop dispensing device including a bottle, a closure, and a cover containing an eye-positioning section and an exit port pin.

FIG. 7b illustrates the cover in the stored position.

FIG. 7c illustrates the cover rotated from the stored position to open the exit port.

DETAILED DESCRIPTION

A closure without moving parts, except for the cover, is described herein. The closure is capable of delivering an accurate volume of liquid. The closure enables a user to apply liquid eye drops with one hand, while the user maintains the head erect and a level gaze. A precise volume of liquid can be consistently administered, regardless of the level of liquid in the container. The device cover ensures sterility and safety since it has no sharp corners or pointed edges. The device is small, portable and disposable.

Before describing the device, several mathematical relations will be presented. These mathematical equations describe the behavior of a liquid when exposed to a hydrophilic (wettable) surface and a hydrophobic (non-wettable) surface. Most clean plastic materials, e.g. polyethylene, are hydrophilic while very few, e.g. Teflon, are hydrophobic.

Figure 1:
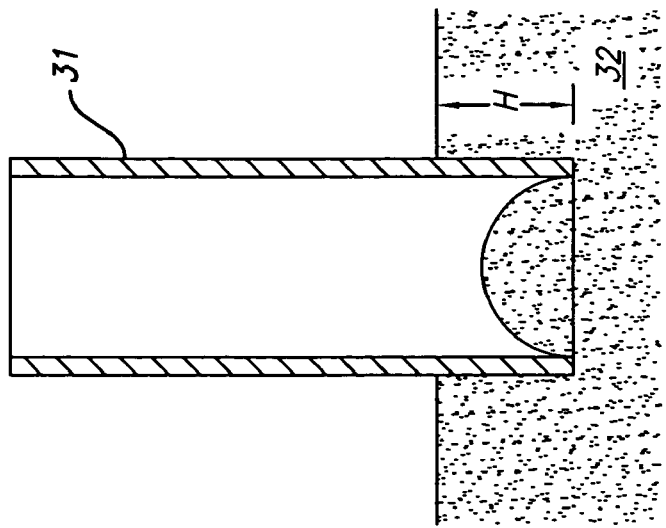
FIG. 1 is a side elevational cross-sectional view of a hydrophilic portion of a tube in a liquid bath.

FIG. 1 is a vertical sectional view of a circular tube 10 having both ends open and immersed in a liquid bath 11. In this example, the adhesive forces of the liquid molecules to the tube surface are greater than the cohesive forces of the liquid (i.e. there is a greater attraction of the liquid to the surface than between the particles of the liquid). Such a tube is described as hydrophilic since the liquid wets it. The height at which the liquid will rise in the hydrophilic portion above the level in the liquid bath may be calculated by equating the force in the upward direction (surface tension force) to the force in the downward direction (gravity weight force). The balance-of-forces becomes:

Force upward=Force downward.

$\pi D s \cos \theta = \pi (D^2/4) H d$ or $H = 4s \cos \theta / Dd$     (1)

where
  D=Internal Diameter of the tube 10,
  d=density of the liquid,
  H=Height to which the liquid will rise,
  s=surface tension of the liquid,
  θ=angle of the liquid surface with the tube surface.

(In the case of many liquids such as water, ethyl alcohol, olive oil or eye drop fluids, the angle of contact, θ, between the liquid and clean glass or most clean plastics is close to zero degrees and the meniscus is approximately hemispherical.)

Figure 2:
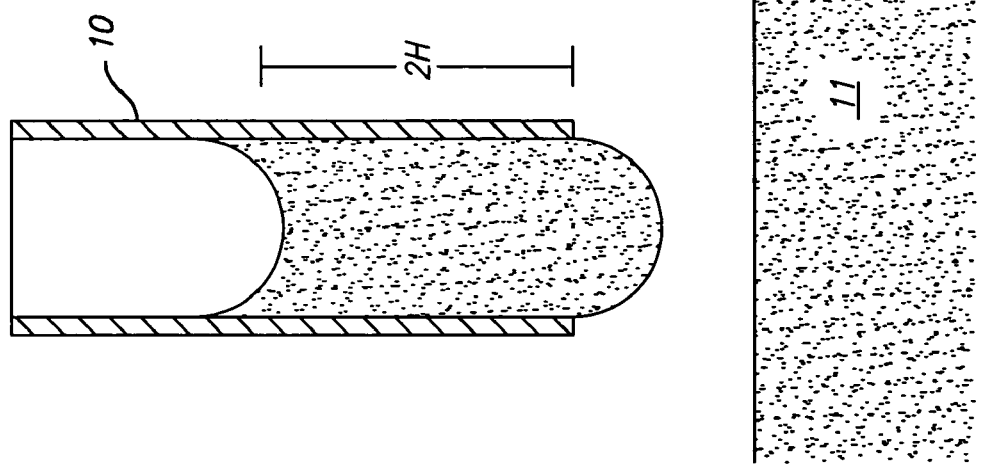
FIG. 2 illustrates the hydrophilic portion withdrawn from the bath.

If the tube 10 were withdrawn from the liquid bath 11, as illustrated in FIG. 2, the height of the liquid that could be retained in the tube 10 would be almost two times the value calculated when the tube 10 was immersed in the liquid. This added height of liquid would occur because, in addition to the surface tension force at the top of the liquid, there is an equal added surface tension force at the bottom of the tube 10. The result is that twice the height of liquid can be retained in the tube 10 when removed from the bath 11.

Figure 3:
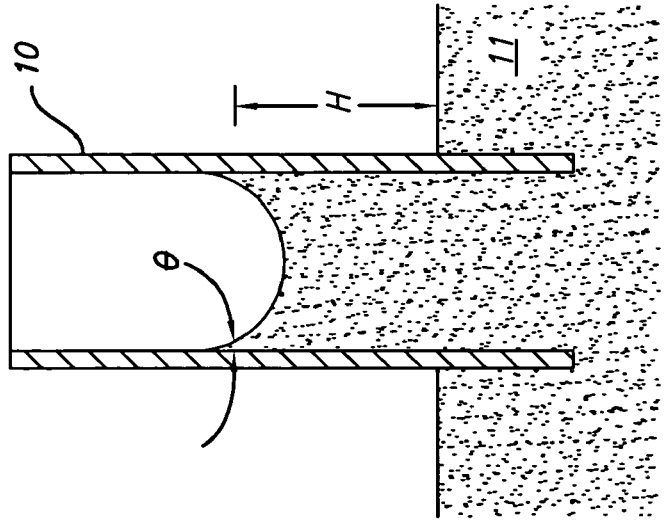
FIG. 3 is a side elevational cross-sectional view of a hydrophobic portion of a tube in a liquid bath.

FIG. 3 is a vertical sectional view of a small circular tube 31 that is immersed in a liquid bath 32. The tube 31 has a hydrophobic portion, thus liquid does not wet the hydrophobic portion of the tube 31. In this example, the upward force is the pressure within the liquid acting on the cross-sectional area of the tube 31 at the liquid air interface within the tube and the downward force is that due to the surface tension force that tends to prevent the liquid from entering the tube 31. Neglecting the small change over the meniscus, the balance of forces in this case becomes:

Force upward=Force downward.

$\pi(D^2/4)Hd=\pi Ds \cos \theta$ or $H=4s \cos \theta/Dd$. (2)

The liquid in the hydrophobic portion of the tube 31 will be a distance below the liquid level in the bath 32 (as indicated by equation 2) by the same amount as the liquid was above the level of the liquid in the bath 11 in the hydrophilic portion of the tube 10 (as indicated by equation 1).

With this background, a device according to the present invention will now be described. The device is not limited to any particular application. For purposes of illustration, the device will be described below in connection with dispensing eye drops.

Figure 4:
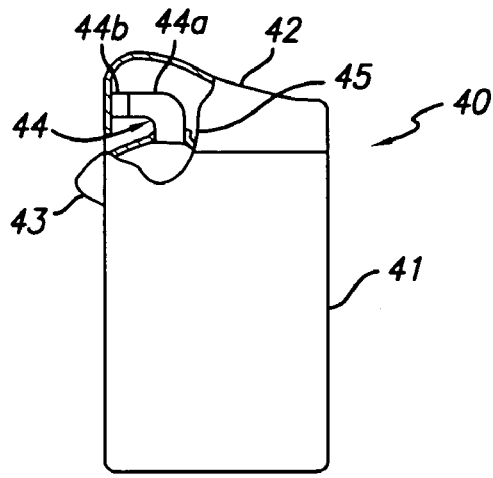
FIG. 4 illustrates an eye drop dispensing device including a container, a container closure, a dispensing tube, and an eye-positioning section on the container.

FIG. 4 illustrates the device 40, which includes an eye drop container 41, a cover 42, and a closure 45, which includes a dispensing tube 44. The dispensing tube 44 is made up of a hydrophilic portion 44a and a hydrophobic portion 44b. An eye-positioning section 43 (detail described later) on the container 41 positions the eyelid using only one hand without having to touch the face with fingers. Also as will be described further below, when the container 41 is inverted, liquid flows freely into the hydrophilic portion 44a. The internal diameter and the length of the hydrophillic portion 44a determine the size of the internal volume and, consequently, the volume of liquid that will be contained therein. If the dispensing tube 44 were fabricated entirely of hydrophilic material, liquid from the container 41 would flow out of the hydrophilic portion 44a until the pressure in the container 41 decreases an amount sufficient to create a vacuum. However, the hydrophobic portion 44b is located at the distal end of the dispensing tube 44 to limit the amount of liquid that enters the hydrophilic portion 44a. The hydrophobic portion 44b illustrated in FIG. 4 is fabricated from a hydrophobic material such as Teflon. As such, liquid will not wet the surface of the hydrophobic portion 44b and liquid is restrained from entering the hydrophobic portion 44b from the hydrophilic portion 44a when the size of the hydrophobic portion 44b is defined by equation 2.

The contoured section 43 accomplishes four tasks:

(1) It opens the lower eye conjunctival sac to form a "well" to hold the eye drop.

(2) It maintains user's hand steady when operating the device 40.

(3) It prevents closing of the lower eyelid when dispensing eye drops.

(4) It helps to aim the dispensing exit orifice located at the distal end of hydrophobic portion 44b.

As illustrated in FIG. 5, in operation, before dispensing any liquid, the container 41 is inverted, first causing the liquid therein to flow into the hydrophilic portion 44a by the forces of gravity and surface tension. FIG. 6a illustrates, in greatly enlarged scale, that the liquid enters the hydrophilic portion 44a but is prevented from flowing into the hydrophobic portion 44b by the combined actions of both the hydrophilic portion 44a and the hydrophobic portion 44b. The surface tension force at the entrance of the hydrophobic portion 44b tends to prevent liquid from entering and the surface tension force at the interface of the hydrophilic portion 44a tends to hold the liquid within the hydrophilic portion 44a. The result is that the liquid is trapped in the hydrophilic portion 44a and does not leak out, regardless of the orientation of the device 40.

FIG. 6b illustrates the dispensing tube 44 when the container 41 is returned to the upright position. A fixed quantity of liquid is held equal to the internal volume of the hydrophilic portion 44a as long as the dimensions satisfy equation (1). When the container 41 is squeezed, the pressure within the container 41 is increased and the pressure of the air contained therein causes the liquid in the hydrophilic portion 44a to be expelled out an exit orifice 44c (at the distal end of the tube 44) through the hydrophobic portion 44b. The liquid is dispensed when the pressure force of the air is greater than the surface tension forces in the hydrophilic portion 44a and the hydrophobic portion 44b.

Figure 4A:
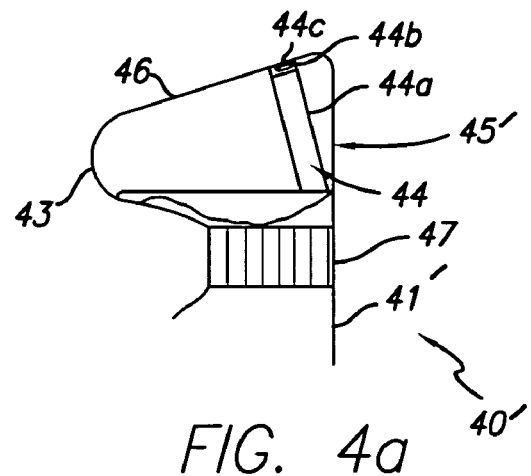
FIG. 4a is a side elevational cross-sectional view of a closure including an eye-positioning section.
Figure 4B:
FIG. 4b is a top view of the closure including an eye-positioning section.
Figure 4C:
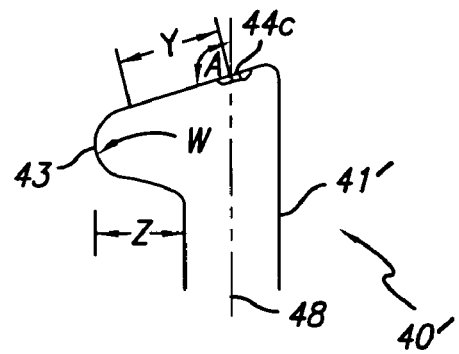
FIG. 4c is a side elevational view of the closure including an eye-positioning section.

FIGS. 4a-4c show a device 40' with an alternative closure 45'. The contoured eye-positioning section 43 is formed on the closure 45' instead of the container 41'. The eye-positioning section 43 is a convex continuation of the angled surface 46 of the top of the closure 45'. The closure 45' is attached to the container 41' by a conventional connector 47. The eye positioning section 43 extends from the exit orifice 44c and protrudes from the neck of the container 41'. Exemplary dimensions for the eye-positioning section 43 are as follows:

(1) Radius (w) of convex surface is 4-7 mm.
(2) Width (x) of convex surface is 8-15 mm.
(3) Angle (A) of surface 46 from exit orifice 44c to convexity is 105-125 degrees from the vertical centerline 48 of the container 41'.
(4) Length (y) of surface 46 from exit orifice 44c to convexity is 10-20 mm.
(5) Protrusion (z) of convex surface from neck of container 41' is 5-15 mm.

In addition, the convex surface may be serrated or textured to improve the grip.

Figure 4D:
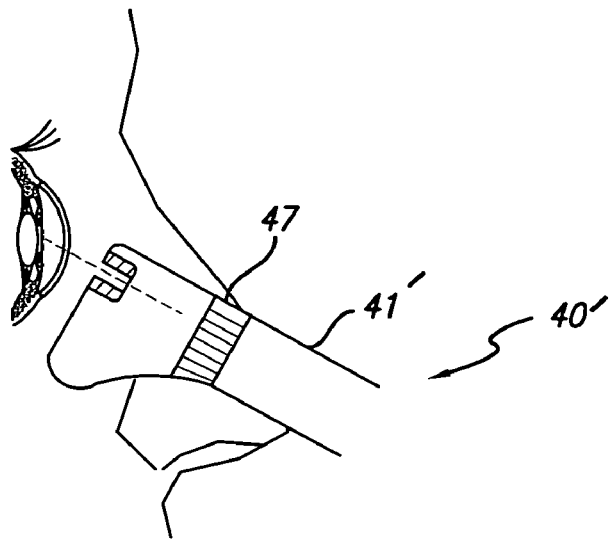
FIG. 4d is a view of the closure including an eye-positioning section in operation.

FIG. 4d illustrates the closure 45' in operation. The device is held substantially upright in a vertical position and the convex surface of the eye-positioning section 43 is brought into firm contact with the skin of the lower eyelid. While the bottom of the device is rotated upward, the contoured section 43 is rotated and moved downward, thereby depressing and fixing the lower eyelid against the cheekbone. (This action also opens the lower conjunctival sac by pulling the lower eyelid away from the eye.) At the same time, the exit orifice 44c is brought to within 5-10 mm. of the eye surface, and the dispensing tube 44 is oriented approximately perpendicular to the eyeball. At this moment, a drop of eye medicament is dispensed.

Figure 7D:
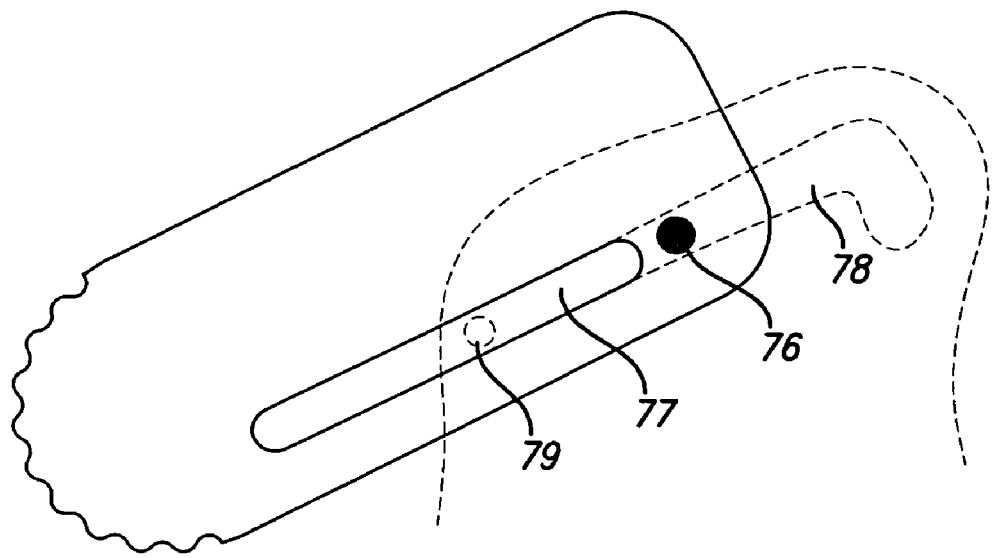
FIG. 7d illustrates the cover midway between the stored and open positions.

FIGS. 7a-7e illustrate an eye drop dispenser 70 including a closure 72 and a cover 71 for the closure 72. The cover 71 is illustrated in solid lines and the closure 72 is illustrated in phantom. The cover 71 has a contoured section 73 similar to the ones described previously and illustrated in FIGS. 4a-4d. FIG. 7a illustrates the cover 71 in the closed position on the closure 72. A protrusion 74 mates with the exit orifice 75 of the closure 72 to seal the interior of the container 41 (the orifice 75 is not visible in FIG. 7*a*, since the protrusion 74 covers it).

FIGS. 7*b*-7*e* illustrate the cover 71 shown in solid lines in various positions while being opened. The closure 72 is shown in phantom. A pin 76 and a groove 77 in the cover 71 mate with a groove 78 and pin 79 in the closure 72. The pin 76 in the cover 71 rides in the groove 78 in the closure 72 while the pin 79 in the closure 72 rides in the groove 77 in the cover 71. (For clarity, the protrusion 74 in the cover and the exit orifice 75 in the closure 72 are not shown.)

FIG. 7*a* illustrates the cover 71 in a stored position.

FIG. 7*b* illustrates the cover 71 rotated to remove the protrusion 74 (not shown) from the exit orifice 75 (not shown). This movement can be performed using only one hand.

FIG. 7*c* illustrates the cover 71 in the partially opened position. The pin 76 has slid along the grove 78 in the closure 72. This movement also can be performed using only one hand.

FIG. 7*d* illustrates the cover position when the pin 79 has moved into groove 77 in the cover 71.

Figure 7E:
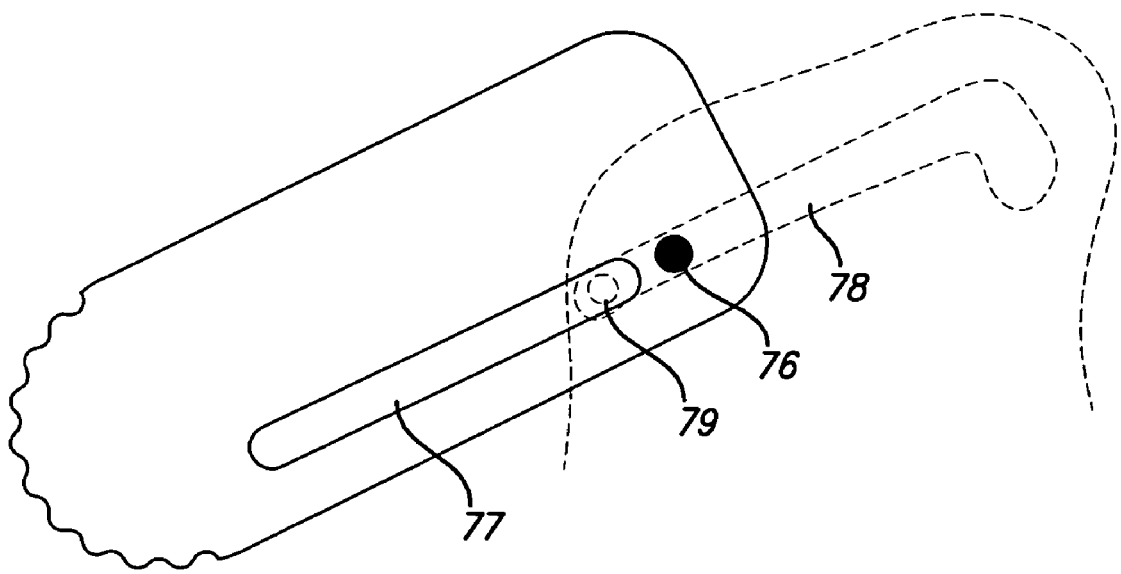
FIG. 7e illustrates the cover in a fully open position.

FIG. 7*e* illustrates the cover 71 in the fully open position. The two pins 76 and 79 in grooves 78 and 77 prevent the cover 71 from rotating thereby providing a stable force to position the eyelid.

Figure 8:
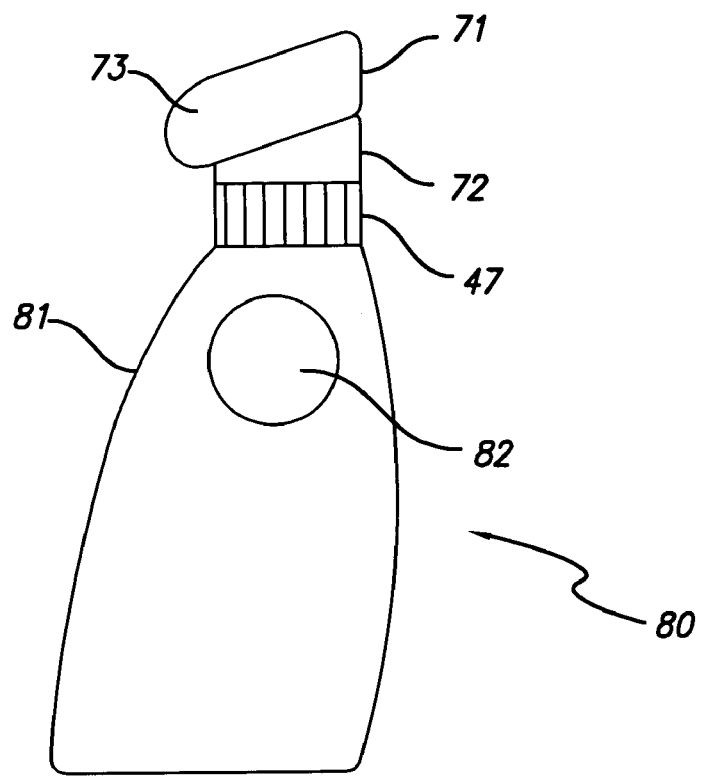
FIG. 8 illustrates a rigid walled container with a flexible button and cover of FIG. 7.

FIG. 8 illustrates another device 80 with a container 81 having rigid walls and a flexible button 82. The external surface of the button 82 is convex and is integral with the container 81. The button 82 is stable only in a normal position or a depressed position. As a result, the button 82 snaps between the two positions when depressed. The purpose of the button 82 is to provide with each use a substantially reproducible increase in pressure to discharge the contents regardless of varying pressure applied to the button or of the amount of liquid in the container 81. The button 82 may have walls that are considerably thinner than the main body of the container 81 so that it can be depressed easily without depressing the main body of the container 81. The change in the internal volume of the container 81 is equal to the change in the internal volume of the button 82 from the normal position to the depressed position (hereinafter button volume). Experiments have indicated that a button volume that equals approximately twenty-five percent of the internal volume of the container will perform well. With a firm force applied, the button will "snap" into the depressed position. Since the temperature of the container 81 remains substantially constant as the button 82 is depressed, the change in the pressure within the container 81 is directly proportional to the change in the internal volume of the button 82. The container 81 is typically filled only to approximately fifty percent of the available volume. The internal volume of the container 81 is very large compared to the button volume. As a result, the increase in pressure within the container 81 will be always nearly constant as the result of depressing the button 82. This is true when the container 81 is fifty percent full or when it is substantially empty. Consequently, the pressure for discharging the controlled volume of liquid will be substantially constant. The result is that the velocity of the discharged liquid also will be substantially constant.

Figure 9:
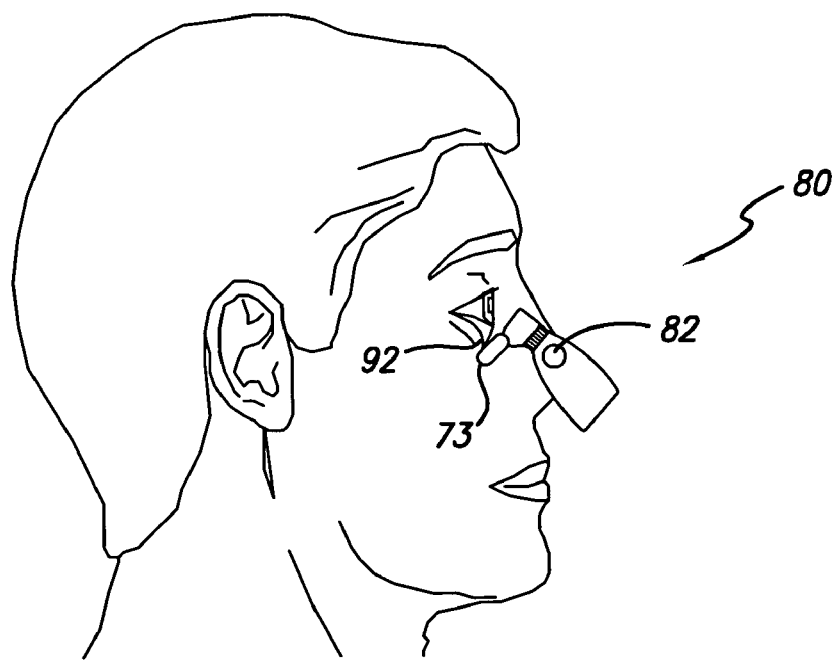
FIG. 9 illustrates the dispenser of FIG. 8 in use.

FIG. 9 illustrates the dispenser 80 of FIG. 8 in use after being inverted to fill the hydrophilic portion. In operation, the contoured portion 73 is placed firmly against the lower eyelid 92 of a patient. Using a rotational motion of the dispenser 80, the lower eyelid 92 is depressed and fixed by the contoured portion 73, which also serves to stabilize the dispenser 80 and orient the exit orifice. The user then depresses the button 82 and dispenses a controlled size of drop of medicament onto the eye. Only one hand of the user is used to hold the dispenser 80 and position the eyelid 92. The patient's head is held substantially upright. After dispensing the drop of the medicament, the user merely inverts the device 80 to refill the hydrophilic portion for the next use.

In the embodiments above, some of the liquid that is contained in the dispensing tube tends to be withdrawn to wet the bottom of the closure around the entrance to the dispensing tube. Under some conditions, this liquid falls back into the container. This fall-back liquid will occur if the amount of liquid in the dispensing tube that flows onto the bottom of the closure is greater than the amount that the surface tension of the liquid can support.

FIGS. 10-13 illustrates several closures 90-96 that prevent the liquid from flowing onto the closure bottom. In each of these closures 90-96, the hydrophilic portion of the dispensing tube 44 has a diameter equal to no more than eight times the product of the liquid surface tension times the cosine of the contact angle, divided by the product of the length of the hydrophilic portion of the dispensing tube and the density of the liquid being dispensed. The hydrophobic orifice of the dispensing tube 44 has a diameter of no more than four times the product of the liquid surface tension times the cosine of the contact angle, divided by the product of the height of the liquid above the orifice when the closure 90-96 is inverted and the density of the liquid.

Figure 10:
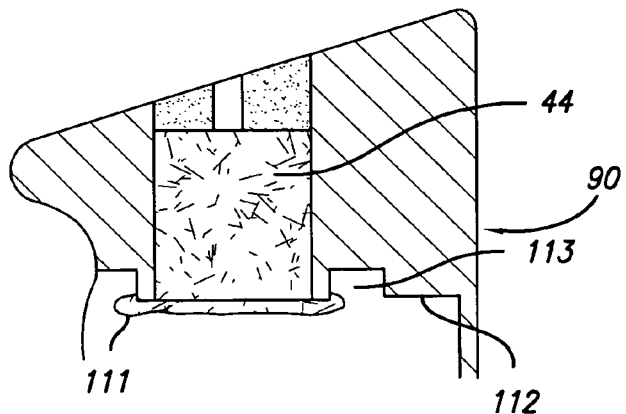
FIG. 10 illustrates a closure with a groove for preventing wetting of the bottom of the closure.

FIG. 10 illustrates a closure 90 with a groove 113 surrounding the fluid entrance of the dispensing tube 44. This closure 90 provides a fixed quantity of liquid in the dispensing tube 44. However, it will prevent the amount of liquid in the groove 113 around the dispensing tube 44 from entering the dispensing tube 44 when the device is inverted and it is being filled. The result is that this small quantity of liquid can not be discharged from the container. The width and depth of the groove 113 depends on the surface tension of the liquid being dispensed. For example, a liquid having a high surface tension will wick across a small groove and wet the bottom. To prevent the wicking, the groove 113 should be at least one millimeter deep and at least one millimeter wide. The groove 113 should be spaced at least one millimeter away from the entrance to the dispensing tube 44.

Figure 11:
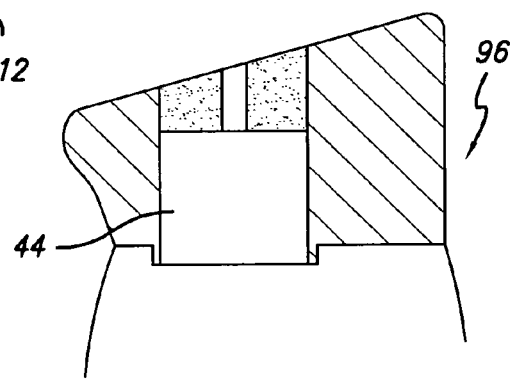
FIG. 11 illustrates a closure and a dispensing tube that extends above the closure.

Conversely, the same situation can be accomplished by the closure 96 shown in FIG. 11. The closure 96 of FIG. 11 does not have a groove. Instead, the dispensing tube 44 extends out of the closure a distance greater than the amount that the liquid wicks up the side.

Figure 12:
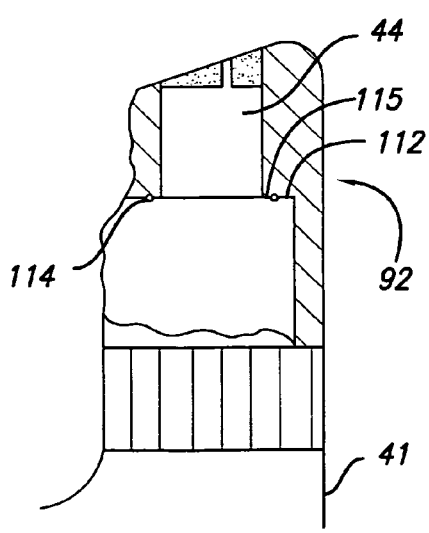
FIG. 12 illustrates a closure with a hydrophobic ring for preventing wetting of the bottom of the closure.

FIG. 12 illustrates another closure 92 for preventing liquid from leaving the dispensing tube 44 by flowing to the closure bottom 112. The dispensing tube 44 has a hydrophobic ring 114 near its entrance that allows only a small quantity of liquid in the dispensing tube 44 to wick from the dispensing tube to the bottom of the closure 92. In effect, the hydrophobic ring 114 replaced the groove 113 of FIG. 10. The width of the hydrophilic surface 115 between the entrance to the dispensing tube 44 and the hydrophobic ring 114 determines the quantity of liquid that can wick from the dispensing tube 44. This wicking condition is similar to the closure 90 of FIG. 10.

Figure 13:
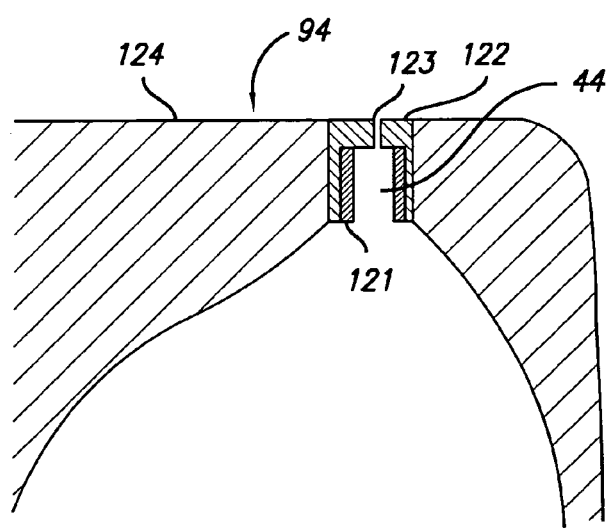
FIG. 13 illustrates a closure with hydrophilic and hydrophobic pieces for preventing wetting of the bottom of the closure.

FIG. 13 illustrates a closure 94 in which a hydrophilic piece 121 is inserted into a hydrophobic piece 122, which in turn is inserted into a body 124 of the closure 94 The thickness of the hydrophilic piece 121 corresponds to the surface 115 of FIG. 12 and the opening 123 in the hydrophobic piece 122 corresponds to the exit orifice 44*c* of FIG. 5. The hydrophilic piece 121 and the hydrophobic piece 122 may have circular or non-circular cross-sections (a circular cross-section is shown in FIG. 13).

The present invention is not limited to the embodiments just described. Modifications and variations may be made without departing from the scope of the appended claims.

We claim:

1. A fluid dispenser closure comprising a tube including a tubular hydrophilic portion and a tubular hydrophobic portion, the hydrophobic portion having an exit orifice at a distal end of the tube.

2. The closure of claim 1, wherein the closure is designed to dispense a liquid; and wherein the hydrophilic portion has an internal diameter no more than four times a product of liquid surface tension times cosine of contact angle and divided by a product of length of the hydrophillic portion and density of the liquid.

3. The closure of claim 1, wherein the closure is designed to dispense a liquid; and wherein the exit orifice in the hydrophobic portion has an internal diameter no more than four times a product of liquid surface tension times cosine of contact angle and divided by a product of height of the liquid above the orifice when the closure is inverted and the density of the liquid.

4. The closure of claim 1, further comprising a cover that can be rotated to open and slide to an operating position.

5. The closure of claim 4, wherein the cover includes a pin that mates with a groove in the closure, and the closure includes a pin that mates with a groove in the cover, whereby when the cover is opened the pin in the cover rides in the groove in the closure while the pin in the closure rides in the groove in a container.

6. The closure of claim 4, wherein the cover has a protrusion to mate with the orifice in the closure.

7. The closure of claim 1, further comprising an eye-positioning section.

8. The closure of claim 7, wherein the eye-positioning section has a convex surface that is serrated or textured.

9. The closure of claim 1, further comprising means for reducing wetting at a bottom of the closure.

10. The closure of claim 9, wherein the means includes a groove around a fluid entrance end of the tube.

11. The closure of claim 9, wherein the means includes a hydrophobic ring around a fluid entrance end of the tube.

12. The closure of claim 9, wherein the means includes a hydrophilic piece inserted into a hydrophobic piece, the hydrophobic piece inserted into a body of the closure, the hydrophobic piece having an orifice.

13. A closure for a container, the closure comprising a dispensing tube including a portion made of a hydrophilic material, an exit orifice of hydrophobic material, and a ring of hydrophobic material near a fluid entrance end of the hydrophilic portion.

14. The closure of claim 13, wherein the dispensing tube includes a hydrophilic insert into a hydrophobic piece, the piece forming both the exit orifice and the entrance to the insert.

15. The closure of claim 13, wherein the closure is designed to dispense a liquid; and wherein the hydrophilic portion of the dispensing tube has a diameter equal to no more than eight times a product of liquid surface tension times cosine of contact angle, divided by a product of length of the hydrophilic portion of the dispensing tube and density of the liquid; and wherein the hydrophobic orifice has a diameter of no more than four times a product of liquid surface tension times cosine of contact angle, divided by a product of height of the liquid above the orifice when the closure is inverted and the density of the liquid.

16. A closure for a container, the closure comprising a dispensing tube made of hydrophilic material surrounded at its entrance by a groove and an orifice made of hydrophobic material located at the exit to the dispensing tube.

17. The closure of claim 16, wherein the closure is designed to dispense a liquid; wherein the hydrophilic portion of the dispensing tube has a diameter equal to no more than eight times a product of the liquid surface tension times the cosine of contact angle, divided by a product of the length of the hydrophilic portion of the dispensing tube and the density of the liquid; and wherein the hydrophobic orifice has a diameter equal to no more than four times a product of the liquid surface tension times the cosine of contact angle, divided by a product of height of the liquid above the orifice when the container is inverted and the density of the liquid.

18. A closure for a container, the closure comprising a dispensing tube made of hydrophilic material, said tube extending from the bottom of the closure and an orifice made of hydrophobic material located at an end of the dispensing tube.

19. The closure of claim 18, wherein the closure is designed to dispense a liquid; wherein the hydrophilic portion of the dispensing tube has a diameter of no more than eight times the product of liquid surface tension times cosine of contact angle, divided by product of the length of the hydrophilic portion of the dispensing tube and the density of the liquid; and wherein being the hydrophobic orifice has a diameter equal of no more than four times a product of liquid surface tension times cosine of contact angle, divided by a product of height of the liquid above the orifice when the closure is inverted and the density of the liquid.

20. The closure of claim 1, wherein surface tension of the hydrophobic portion alone causes liquid to be retained within the hydrophilic portion when the tube is inverted.

* * * * *